United States Patent [19]
Davis et al.

[11] Patent Number: 5,750,791
[45] Date of Patent: May 12, 1998

[54] NITRIC ACID HYDROLYSIS OF POLYAMIDES

[75] Inventors: Darwin Darrell Davis; Eugene Dennis Wilhoit, both of Victoria. Tex.

[73] Assignee: E. I. du Pont de Nemours and Company, Wilmington. Del.

[21] Appl. No.: 697,116

[22] Filed: Aug. 20, 1996

Related U.S. Application Data

[63] Continuation of Ser. No. 493,836, Jun. 22, 1995, abandoned.
[51] Int. Cl.$^6$ .................................................. C07C 209/62
[52] U.S. Cl. ............................................ 564/488; 562/512
[58] Field of Search ................................ 564/488; 562/512

[56] References Cited

U.S. PATENT DOCUMENTS

| | | | |
|---|---|---|---|
| 3,069,465 | 9/1962 | Monet | 260/537 |
| 3,592,854 | 7/1971 | Potts et al. | 260/583 |
| 5,410,082 | 4/1995 | Pfirmann | 564/414 |
| 5,457,197 | 10/1995 | Sifniades et al. | 540/540 |

FOREIGN PATENT DOCUMENTS

WO 94/13616  6/1994  WIPO ................... C07C 55/12

*Primary Examiner*—Brian M. Burn

[57] ABSTRACT

Dicarboxylic acid and diamine are recovered from polyamides by hydrolysis with nitric acid, followed by separation of the dicarboxylic acid, and hydrogenation of the nitric acid, and then recovery of the diamine.

12 Claims, 1 Drawing Sheet

NITRIC ACID HYDROLYSIS OF POLYAMIDES

This is a continuation of application Ser. No. 08/493,836 filed Jun. 22, 1995, now abandoned.

FIELD OF THE INVENTION

The present invention concerns a process for recovering constituent monomers from polyamides. More specifically, polyamides are hydrolyzed into their constituent monomers in a nitric acid solution. The nitric acid is then converted to ammonia via hydrogenation, thus freeing the amine components and avoiding the formation of inorganic salts.

BACKGROUND OF THE INVENTION

Disposal of polymeric materials in landfills is becoming increasingly costly, as landfill areas reach capacity and available land areas become more limited. Condensation polymers, including polyamides, are among those materials widely disposed of in landfills. Polyamide carpets of nylon 66, and nylon 6, and other molded parts are major contributors to landfill. However, polyamides can be reclaimed because they may be degraded to their monomeric components, usually by hydrolysis. U.S. Pat. No. 3,069,465 describes a sulfuric acid-catalyzed process for hydrolysis of nylon 66, in which the acid is neutralized with calcium hydroxide to free the amine. A large waste stream of calcium sulfate is the co-product. A second approach is described in U.S. European Chemical News, Jun. 29, 1992, p. 28, whereby base-catalyzed hydrolysis of nylon produces the salt of the monomer acid, which is then electrolyzed to free the acid and circumvent the salt disposal problem. An economical process for reclaiming the ingredients from nylon polyamide without generating a major waste stream in itself remains a goal of the industry.

Published International PCT Application WO 94/13616 describes a method of treating polyamides by oxidative hydrolysis of the amide groups in the presence of nitrous groups. For example, oxidative hydrolysis of nylon 66 results in recovery of adipic acid and oxidation of the diamine to adipic, glutaric, and succinic acids. The diamine is not isolated from the reaction mixture but rather is oxidized in the hydrolysis medium, to a mixture of diacids or degraded into C, $CO_2$, $H_2O$, and CO.

It is an object of the current invention to provide a method for hydrolyzing polyamide materials in nitric acid solutions while avoiding significant oxidation of the diamine. The polyamides are thus substantially converted to their constituent acid and amine components, capturing most of the monomer value. The recovered monomers may be used to produce polyamides having properties comparable to the original polyamide. It is a further object of the invention to provide a process for the acid hydrolysis of polyamides which avoids the formation of a salt waste stream.

SUMMARY OF THE INVENTION

The present invention is a process for the recovery of diamine and dicarboxylic acid from a polyamide condensation product of the diamine and the dicarboxylic acid which comprises:

a) forming a reaction mixture containing the polyamide condensation product in 10 to 35 wt % nitric acid where the amount of nitric acid is, on a molar basis, stoichiometrically in excess of the diamine content;

b) hydrolyzing the polyamide condensation product at a temperature in the range of about 70°–110° C.; thus forming a reaction product containing diamine and dicarboxylic acid;

c) separating dicarboxylic acid from the reaction product;

d) catalytically hydrogenating nitric acid in the portion of the reaction product remaining after step c) to form ammonia; and e) recovering diamine from the product of step d).

BRIEF DESCRIPTION OF THE DRAWING

The DRAWING is a flow diagram of an embodiment of the process of the invention.

DETAILED DESCRIPTION

Figure 1:
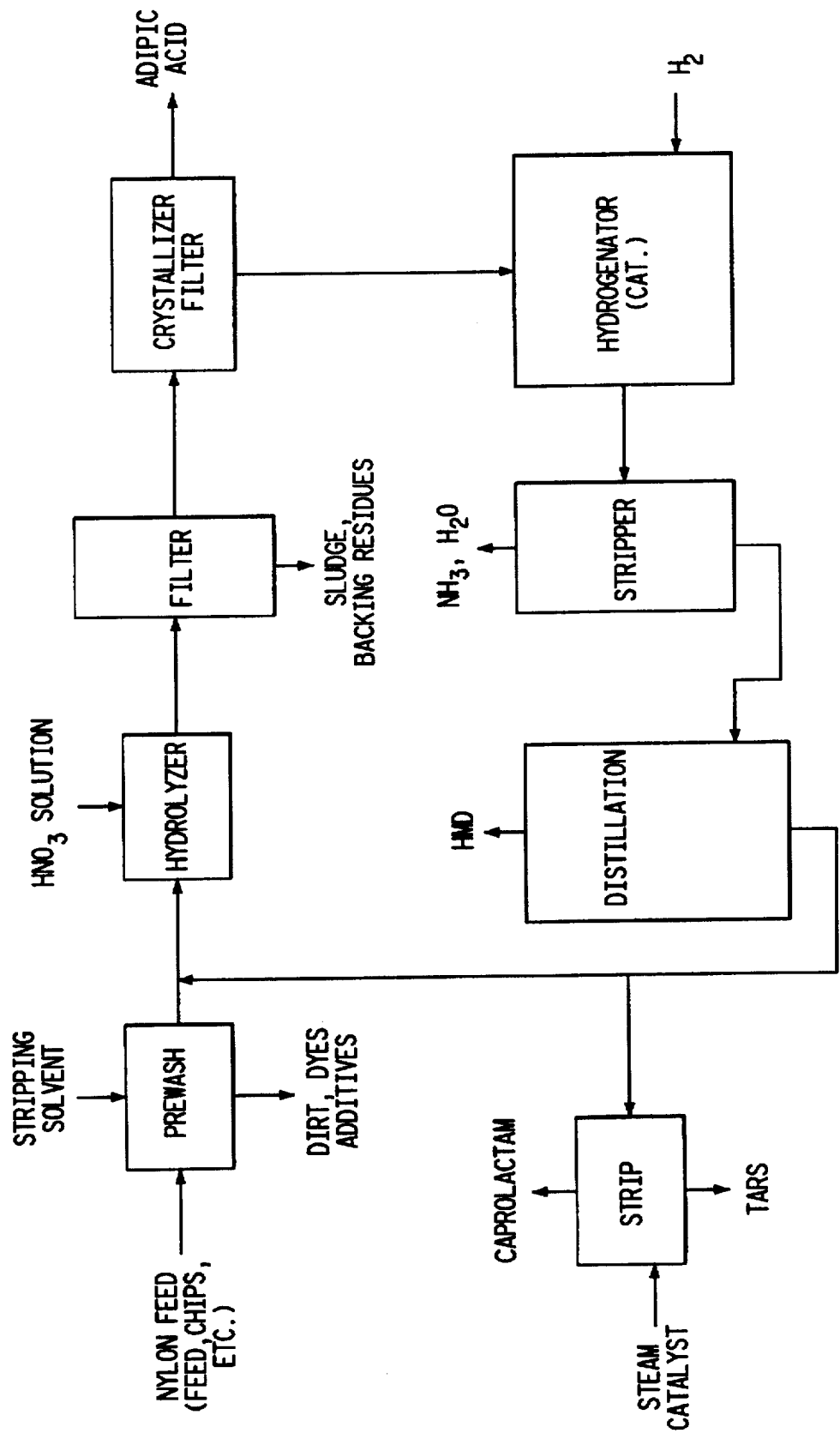

The process of the current invention involves a hydrolysis step in which a polyamide-containing material is hydrolyzed in a nitric acid solution under conditions which avoid significant oxidation of the diamine, followed by a hydrogenation step in which the nitric acid is converted to ammonia by reaction with hydrogen in the presence of a hydrogenation catalyst, thereby avoiding the salt formation step necessary to release the amine products in prior art processes. The oxidation of the diamine component of the polyamide seems to occur primarily when the diamine components are still in the amide form: that is, before the diacid component and diamine component have formed by the hydrolysis of the polyamide.

The process may be applied to polyamides which are obtained by condensation of diacids and diamines or polyamine copolymers which are the condensation product of lactams or aminoacids with diamines and dicarboxylic acids, or mixtures thereof. Polyamides which may be recycled into monomers using the process of the current invention include homopolyamides obtained from the condensation of a single diamine and a single diacid and copolyamides obtained by condensation of a mixture of two or more diamines with one or more diacids or a mixture of two or more diacids with one or more diamines. Examples of polyamides include those obtained from diamines selected from the group consisting of aliphatic, alicyclic, and aromatic diamines having 4–16 carbon atoms and diacids selected from the group consisting of aliphatic, alicyclic, and aromatic dicarboxylic acids having 4–16 carbon atoms. Suitable diacids include adipic acid, suberic acid, azelaic acid, terephthalic acid, and isophthalic acid. Suitable diamines include tetramethylene diamine, pentamethylene diamine, hexamethylene diamine (HMD), phenylenediamine, and piperazine.

The process is especially useful for recycling of nylon 66, or mixtures of nylon 66 and nylon 6 which are commonly used in textile articles such as carpets or in molded products such as automobile components. Such articles may be processed to provide a fiber or chip feed to the hydrolysis step of the current invention. It is generally unnecessary to remove additives which may be contained in these articles such as finishes, pigments, fillers, glass fibers, etc. However, if the additives are present in significant levels and react with nitric acid, it is desirable to remove the bulk of the filler. For example, in recycle of carpeting materials, it is generally necessary to remove the bulk of the backing, including binder and filler. The calcium carbonate filler reacts with nitric acid to neutralize it and produce carbon dioxide, and the styrene-butadiene rubber used as a binder tends to react with nitric acid to prematurely initiate oxidation.

Best results in the hydrolysis of nylon 66 are obtained in a limited nitric acid concentration range. Below about 18 wt % nitric acid, nylon exists in the solid phase at the atmospheric pressure boiling temperature (103°–104° C.) of the mixture, slowly dissolving as hydrolysis proceeds. If the concentration is increased to 25 wt % or more, nylon readily melts in the range 70°–100° C. This greatly facilitates the charging of bulky nylon fiber feed to a hydrolysis reactor. Higher solubility and higher hydrolysis rates are also achieved with the higher acid concentration. On the other hand, higher concentrations ions of nitric acid can lead to the slow initiation of oxidation of the amide, resulting in the destruction of the amine portion of the molecule. Satisfactory hydrolysis may be carried out in 10–35 wt % nitric acid, preferably 15–35 wt %, and more preferably 18–30 wt % nitric acid. The hydrolysis may be carried out at temperatures up to the atmospheric pressure boiling point of the system as defined by the water, acid, and dissolved organics. Preferably, the hydrolysis is carried out at temperatures of 70°–110° C., more preferably 103°–106° C. Nitric acid concentration is calculated based on the weight of water and nitric acid in the solution.

Oxidation can be further controlled by several means. For example, maintaining boiling in the hydrolysis reactor effectively strips traces of NOx at marginal acid concentrations, circumventing the development of significant concentrations of nitrous acid, the oxidation initiator. Attempts to increase hydrolysis rate at lower concentrations (<15 wt %) of nitric acid by increasing pressure and temperature was found to result in oxidation. Oxidation also can be avoided by using a two-stage reactor in which a first stage at higher nitric acid concentration (e.g., 25–35 wt %) is used to melt and dissolve the nylon, followed by a second stage in which the nitric acid is diluted to a concentration which does not cause oxidation (e.g., 10 to 20 wt %) prior to hydrolysis. Use of nitrous acid scavengers, such as urea, also suppresses initiation of oxidation. In view of the desirability of using higher nitric acid concentrations to take advantage of its nylon complexing properties, it has been found that oxidation can be avoided if the excess nitric acid (above that required to neutralize the amine function of the polyamide) is limited. Nitric acid concentrations of 25–35 wt % or more can be used if the nylon charge is near the stoichiometric amount. This has the added advantage of providing high concentrations of the hydrolysis products and thus higher recovery in subsequent processing steps. Preferably, the excess nitric acid is less than about 4–6 wt % when using nitric acid concentrations in the 25 to 35 wt % range. When using less concentrated nitric acid, a greater excess is satisfactory. The moles of excess nitric acid is calculated by subtracting the theoretical moles of amine groups from the initial moles of nitric acid charged. The excess nitric acid is obtained by converting the excess moles of nitric acid to grams of excess nitric acid and calculating a weight percent based on the total aqueous acid charge: see Examples 7–11.

When the conversion of polyamide to monomer reaches about 75 wt %, a significant fraction of short chain oligomers and cyclic monomers or dimers remains, some of which hydrolyze relatively slowly. One alternate to the all-hydrolysis mode of the invention is to hydrolyze until the major portion of the material has been converted to monomeric adipic acid, hexamethylenediamine, and/or aminocaproic acid, in the case of nylon 66/nylon 6, then to initiate oxidation to complete the reaction of partially hydrolyzed intermediates. Oxidation can be initiated by adding nitrous group-containing materials, such as sodium nitrite, to the reaction mixture. Preferably, the temperature is kept at 100° C. or less during such an oxidation step so that the recovered yield of intermediates is maximized. Since the oxidation occurs mainly on the amide function, the amine function being relatively stable in the acid medium, the shorter chain linear or cyclic oligomers are oxidized to free the adipic acid and to raise the overall single pass recovery of monomers. The amine portion of the oligomer amide group is largely lost in this reaction.

While the process may be carried out in a safe manner by limiting temperature, pressure, and nitric acid concentration, it should be recognized that the potential for rapid, exothermic gas-generating reactions exists. Testing of the severity of such potential indicates that 100% oxygen balanced mixtures (assuming only $CO_2$, $N_2$, and $H_2O$ products) prepared with make up acid of more than 20 wt % nitric acid concentration present the greatest hazard. Mixtures which limit the "excess" nitric acid as described above are at only approximately 15–25% of oxygen balance.

The advantages of the nitric acid hydrolysis process are best realized with nylon mixtures containing major amounts of nylon 66. Prior art processes for recovery of e-caprolactam work well for nylon 6, but often destroy any nylon 66 components which may be present. FIG. 1 is a schematic representation of an embodiment of the current invention, as applied to the recycling of a mixed feed of nylon 66 and nylon 6. Reclaimed nylon, either as sheared or separated carpet fiber or chopped molded parts, is optionally washed in a pre-wash stage to remove dirt, dyes, etc., then fed to a hydrolyzer, where it is mixed with a solution containing 18–35 wt % nitric acid and heated at reflux. The products of the hydrolysis of N66 are hexamethylene diamine and adipic acid. The product of hydrolysis of nylon 6 is e-aminocaproic acid.

The resulting hydrolysis solution may then be filtered while hot to remove sludge containing bits of carpet backing components, metal salts, fiberglass, etc., and cooled to crystallize the adipic acid. The adipic acid is collected, for example, by filtration, and rinsed with cold water. The adipic acid cake obtained upon cooling and filtering the hydrolysis mixture typically contains 99.5–99.8 wt % adipic acid. It may be refined by recrystallization from water. Depending on the level of contaminants, dyes, additives, carpet backing in the original fiber, as well as any pretreatment it may have had, multiple crystallizations and/or charcoal treatment may be required to produce fiber-grade adipic acid. The largest impurity was found to be hexamethylenediamine. Nylon 66 prepared on a test scale from this adipic acid could not be distinguished from material produced similarly with commercial fiber grade acid.

After crystallization and filtration of adipic acid, the filtrate, which contains hexamethylenediamine, residual adipic acid, aminocaproic acid, and other hydrolysis products, is hydrogenated to destroy the nitric acid by passing over a hydrogenation catalyst under hydrogen pressure. Hydrogenation of nitric acid to ammonia can be carried out with a heterogeneous catalyst, preferably as a slurry in the aqueous solution. The catalyst may be suspended in the aqueous solution by agitation. The catalyst typically is 2–20 wt % of the weight of aqueous solution, although a slurry outside this range could be used. Hydrogenation is typically carried out in the temperature range of 50°–150° C. and hydrogen pressures in the range of 50–1000 psig. Several hydrogenation catalysts can be used and include platinum, palladium, and nickel. For cost effectiveness, platinum and palladium are normally deposited on carbon, alumina, or silica whereas nickel can be used as an alloy, e.g., raney nickel. Several commercial platinum and palladium catalyst on various substrates are effective for this hydrogenation and can be used directly. In a manner similar to that reported for determination of nitrate in water (U.S. Pat. No. 4,526,870), copper addition to the commercial platinum and palladium catalysts enhances the catalytic activity as measured by the rate of hydrogenation of nitric acid per unit weight of catalyst. The copper promoter is deposited on the catalyst surface by addition of a soluble copper salt (such as copper sulfate, acetate, nitrate) to an aqueous solution and hydrogenating at 25°–150° C. and 50–1000 psig for short periods of times, usually 30 minutes to 2 hours. Typically, the copper to precious metal weight ratio on the solid catalyst is in the range of 0.1–1.5. After the promoter is deposited, the hydrogenation of the aqueous nitric acid is carried out as described above.

The hydrogenation conditions are normally such that over 95% of the nitric acid is converted in the first stage of a process. This requires the temperature, pressure, feed rate, and quantity catalyst be optimized or adjusted to achieve this conversion. Optionally, a second stage could be used for higher conversion. Continuous feed of the aqueous solution to the suspended catalyst slurry, with simultaneous removal of the product solution through a 1–10 micron filter, is especially advantageous. High conversions, (>90%) of the nitric acid to ammonia, with only minor losses of catalyst, can be achieved at steady state in this manner.

The filtered aqueous hydrogenation product then is passed to the product recovery system shown in FIG. 1. The ammonia produced during the hydrogenation may be stripped out, and the water removed by distillation. Hexamethylenediamine may then be recovered by distillation (optionally under vacuum). The distillation bottoms may contain residual adipic acid and hexamethylene diamine, aminocaproic acid, and oligomers thereof, depending on the composition of the polyamide feed. This mixture may be returned to the hydrolysis reactor for further recovery of monomers. A portion of the stream is stripped to recover caprolactam, using methods known in the art.

Examples 1–3

A nylon 66 charge comprising sheared face fiber from post-consumer carpet from a variety of sources was placed in a round bottom flask (usually 500 cc) equipped with a reflux condenser, thermometer, magnetic stirrer, and a sample port. The nitric acid solution was then added, and the mixture was heated carefully with mixing to avoid local overheating, via a heating mantle. After refluxing was achieved, samples were periodically removed for analysis. Adipic acid concentration was determined by liquid chromatographic analysis, while hexamethylenediamine and e-aminocaproic acid were determined similarly after derivatization by acetylation. The rate of the hydrolysis reaction increases with nitric acid concentration. The results are summarized below:

| Example No. | HNO₃ Wt. g | Charge %(wt) | Nylon Charge Type | Nylon Charge Wt. g | Reflux Time Hrs. | Conc'n, Wt. % Adipic Acid | Conc'n, Wt. % HMD |
|---|---|---|---|---|---|---|---|
| 1 | 90 | 10 | 6,6 fiber | 10 | 6 | 1.73 | 1.33 |
| 2 | 90 | 15 | " | 10 | 6 | 4.57 | 3.03 |
| 3 | 90 | 18 | " | 10 | 6 | 5.37 | 3.91 |

Example 4–5

The procedure described in Examples 1–3 was followed. Example 4 used a blend of nylon 66 and nylon 6 sheared face fiber from post-consumer carpet, and Example 5 used chopped nylon 66 automotive radiator components. The results are summarized below:

| Example | HNO₃ Wt g. | Charge %(wt.) | Nylon Charge Type | Nylon Charge Wt g. | Reflux Hrs. | Concentration, wt. % Adipic Acid | Concentration, wt. % Amino- HMD | Concentration, wt. % Caproic Acid |
|---|---|---|---|---|---|---|---|---|
| 4 | 90 | 23 | 6,6-Fiber | 15 | 6 | 5.39 | 4.12 | 9.42 |
|   |    |    | 6-Fiber   | 15 |   |      |      |      |
| 5 | 90 | 18 | 6,6-chopped Automotive Radiator (Glass Filled) | 10 | 6 | 3.29 | 2.28 | — |

Example 6

Fifty grams of nylon 66 pellets, 50 g HNO₃, and 220 g H₂O were heated to reflux (approx. 1100° C.) at atmospheric pressure for 5–6 hours. Analysis showed adipic acid and hexamethylenediamine being produced and at the end of 2 hours the solution contained 3.4 wt % adipic acid and 2.8 wt % hexamethylenediamine. At the end of six hours, the solution contained about 9 wt % adipic and 6.9 wt % hexamethylenediamine. Subsequent analysis showed another compound was present and later identified as the cyclic monomer of hexamethylenediamine and adipic acid. After hydrolysis, for six hours, the solution was cooled and solids filtered. The filtrate contained 2.8% adipic acid, and 7.3% hexamethylenediamine, and 18.1% HNO₃. The wet crude adipic acid cake contained about 57% (wt) adipic acid with 3% HNO₃ and 3.3% hexamethylenediamine. The filtrate was used as a continuous feed at 400 ml/hr to a hydrogenation unit (350 psig H₂, 130° C., 10 g 5% Pt/C suspended in 250 cc H₂O). Product analyses showed 71% of the HNO₃ was converted and about 90% of the adipic acid and hexamethylene diamine recovered.

Examples 7–11

This series of examples covers a range of conditions for controlling the onset of oxidation after several hours of heating. The time at which traces of NOx appear in the vapor space, and the HMD concentration growth ceases to occur is noted in Examples 7–11. The experimental procedure is the same as in Examples 1–5. Additionally, the excess of HNO₃ over theoretical diamine is recorded, as well as its equivalent concentration based on the aqueous HNO₃ charged.

| Example | HNO₃ Wt. g | Charge %(wt.) | Nylon 66 Wt.g | Other | Excess Mol | HNO₃ Conc'n (H₂O Basis) | Time Hours | NOx ? | AA | HMD | Cycl. Mon |
|---|---|---|---|---|---|---|---|---|---|---|---|
| 7 | 70 | 23 | 10 | — | .168 | 15 | 5 | No | 6.62 | 4.85 | 1.65 |
|   |    |    |    |   |      |    | 6 | Yes | 8.14 | 5.16 | 0.17 |
| 8 | 90 | 30 | 10 | — | .340 | 24 | 3.7 | Yes | 6.00 | 3.17 | 0.79 |
| 9 | 90 | 25 | 30 | — | .092 | 6.4 | 6 | No | 11.53 | 8.07 | 4.31 |
| 10 | 68 | 30 | 32.5 | — | .036 | 3.4 | 8 | No | 15.7 | 11.9 | 5.20 |
| 11 | 90 | 30 | 10 | 570 ppm urea | .340 | 24 | 6 | No | 5.45 | 4.32 | 1.33 |

Examples 9 and 10 demonstrate how oxidation can be controlled by controlling the amount of excess nitric acid present in the hydrolysis reactor. Example 11 demonstrates the use of urea as a nitrous acid scavenger. There is no evidence of oxidation after 6 hours, as compared to Example 8 where, under similar conditions with no scavenger, NOx was detected in the vapor space after 3.7 hours.

Example 12

This example illustrates the intentional initiation of oxidation after 5 hours of hydrolysis and demonstrates the reduction in cyclic monomer and increase in recovered adipic acid that occurs without significantly affecting the amount of hexamethylene diamine produced. A mixture of 90 g of 23% HNO₃ containing 0.027 g urea and 10 g of nylon 6,6 carpet fiber was heated at reflux for 5 hours (104° C.), then the injection of small amounts of a 5 wt % NaNO₂ solution was begun in order to initiate oxidation. A total of 0.8 cc was added, and the temperature was reduced to 90° C. to cease boiling. Samples were removed for analysis during the next 90 minutes.

| Time | 5 Hr(O) | 20 Min | 40 Min | 60 Min | 90 Min |
|---|---|---|---|---|---|
| % Adipic Acid | 4.52 | 5.06 | 5.78 | 6.28 | 6.29 |
| % HMD | 3.58 | 3.65 | 3.80 | 3.70 | 3.63 |
| % Cyclic Monomer | 1.60 | 1.08 | 0.30 | 0 | 0 |

The oxidation stage has converted the cyclic monomer to adipic acid while not significantly affecting the HMD produced in the first stage, resulting in an overall increase in recovery.

What is claimed is:

1. A process for the recovery of diamine and dicarboxylic acid from a polyamide condensation product of the diamine and the dicarboxylic acid which comprises:

a) forming a reaction mixture containing the polyamide condensation product in 10 to 35 wt % nitric acid where the amount of nitric acid is, on a molar basis, stoichiometrically in excess of the diamine content;

b) hydrolyzing the polyamide condensation product at a temperature in the range of about 70°–110° C.; thus forming a reaction product containing diamine and dicarboxylic acid;

c) separating dicarboxylic acid from the reaction product;

d) catalytically hydrogenating nitric acid in the portion of the reaction product remaining after step c) to form ammonia;

e) and recovering diamine from the product of step d).

2. The process of claim 1 in which the reaction mixture also contains nylon 6.

3. The process of claim 1 in which the polyamide condensation product also contains polymerized units of caprolactam.

4. The process of claim 1 in which step c) includes crystallization and filtration.

5. The process of claim 1 in which the diamine is recovered in step d) by distillation.

6. The process of claim 1 in which after step b), a nitrous group-containing material is added to initiate oxidation of partially hydrolyzed intermediates.

7. The process of claim 6 in which the nitrous group-containing material is sodium nitrite.

8. The process of claim 1 in which a nitrous acid scavenger is present in the reaction mixture to suppress oxidation of the polyamide during hydrolysis.

9. The process of claim 8 in which the nitrous acid scavenger is urea.

10. The process of claim 1 where the excess nitric acid is less than 4–6 wt % of the diamine content, and the concentration of the nitric acid is 25 to 35 wt %.

11. The process of claim 1 in which the concentration of the nitric acid is 18 to 30 wt %.

12. The process of claim 1, wherein the hydrolyzing step (b) occurs at a temperature in the range of 103° to 106° C.

* * * * *